US008562968B2

(12) United States Patent
Günther et al.

(10) Patent No.: US 8,562,968 B2
(45) Date of Patent: Oct. 22, 2013

(54) USE OF STEM CELLS AND CD6 DEPLETED STEM CELLS FOR THE INDUCTION OF TOLERANCE TO ALLOGENIC TRANSPLANTS AND/OR FOR THE TREATMENT OF LEUKEMIA

(75) Inventors: Wolfgang Günther, Planegg (DE); Hans Jochen Kolb, München (DE)

(73) Assignee: GSF-Forshungszentrum für Umwelt und Gesundheit, GmbH, Oberschleißheim (DE)

( * ) Notice: Subject to any disclaimer, the term of this patent is extended or adjusted under 35 U.S.C. 154(b) by 1468 days.

(21) Appl. No.: 10/410,852

(22) Filed: Apr. 10, 2003

(65) Prior Publication Data

US 2003/0232433 A1 Dec. 18, 2003

Related U.S. Application Data

(63) Continuation of application No. PCT/EP01/11776, filed on Oct. 11, 2001.

(30) Foreign Application Priority Data

Oct. 11, 2000 (DE) .................................. 100 50 334

(51) Int. Cl.
*A01N 63/00* (2006.01)
*C12N 5/00* (2006.01)
*C12N 5/08* (2006.01)
*A61F 13/00* (2006.01)

(52) U.S. Cl.
USPC ........................... 424/93.1; 435/325; 435/372

(58) Field of Classification Search
USPC .................................. 424/93.1; 435/325, 372
See application file for complete search history.

(56) References Cited

U.S. PATENT DOCUMENTS

| | | | | |
|---|---|---|---|---|
| 5,199,942 | A | * | 4/1993 | Gillis ........................... 604/4.01 |
| 5,772,994 | A | * | 6/1998 | Ildstad et al. ................. 424/93.7 |
| 6,217,867 | B1 | * | 4/2001 | Ildstad ........................ 424/144.1 |
| 6,447,767 | B1 | * | 9/2002 | Slavin et al. .................. 424/93.1 |
| 6,558,662 | B2 | * | 5/2003 | Sykes et al. ................... 424/93.1 |
| 7,498,023 | B2 | * | 3/2009 | Sykes ........................... 424/93.1 |

OTHER PUBLICATIONS

Kolb et al. CD6-negative blood stem cells facilitating HLA-haploidentical transplantation in the treatment of advanced leukemia. Abstract #889; Blood 96 (11 Part 1): p. 208a, 2000).*
Sehn et al. Comparative outcomes of T cell-depleted and non-T-cell-depleted allogeneic bone marrow transplantation for chronic myelogenous leukemia: Impact of donor lymphocyte infusion. J. Clin. Oncology 17:561-568, 1999.*
Sao et al. A new marrow T cell depletion method using anti-CD6-monoclonal antibody-conjugated magnetic beads and its clinical application for prevention of acute graft-vs.-host disease in allogeneic bone marrow transplantation: results of a phase I-II trials. Int. J. Hematol. 69:27-35, 1999. (Abstract only).*
Soiffer et al. CD6+ T cell depleted allogeneic bone marrow transplantation from genotypically HLA non-idnetical related donors. Biology of Blood and Marrow Tranplantation 3:11-17, 1997.*
Gerrard et al. Toxicity and dosimetry of fractionated total body irradiation prior to allogeneic bone marrow transplantation using a straightforward radiotherapy techniques. Clinical Oncology 10:379-383, 1998.*
Soiffer et al., "CD6-Depleted Allogeneic Bone Marrow Transplantation for Acute Leukemia in First Complete Remission", CD-6 Depleted BMT for Acute Leukemia, Blood, vol. 89 (No. 8), p. 3039-3047, ( Apr. 15, 1997).
Barrett et al., "Effect of nucleated marrow cell dose on relapse and survival in identical twin bone marrow transplants for leukemia", Blood, vol. 95 ( No. 11), p. 3323-3327, ( Jun. 1, 2000).
Champlin et al., "Blood stem cells compared with bone marrow as a source of hematopoietic cells for allogeneic transplantation", Blood, vol. 95 ( No. 12), p. 3702-3709, ( Jun. 15, 2000).
Cahn et al., "Low dose T-cell lymphocyte infusion combined with marrow T-cell depletion as prophylaxis of acute graft vs host disease for HLA identical sibling bone marrow transplantation", Hematology and Cell Therapy, Springer-Verlag (France), p. 31-37, (1999).
Champlin et al., "T-cell depletion of bone marrow transplants for leukemia from donors other than HLA-identical siblings: advantage of T-cell antibodies with narrow specificites", T-Cell Depletion of Alternative Donor Transplants, Blood, vol. 95 ( No. 12), p. 3996-4003, ( Jun. 15, 2000).
Craddock et al., "Estimating leukemia-free survival after allografting for chronic myeloid leukemia: a new method that takes into account patients who relapse and are retored to complete remission", Blood, vol. 96 ( No. 1), p. 86-90, ( Jul. 1, 2000).
Koh et al., *Nonmyeloablative allogenic hematopoietic stem cell transplant using mismatched/haploidentical donors: A review. Blood Cells, Molecules, and Diseases.* vol. 40 pp. 20-24 (2008).
"Magnetic Cell Sorting." CD6 Microbeads: human. pp. 1-3 www.miltenyibiotec.com.
Aversa et al., "Treatment of high-risk acute leucemia with T-cell-depleted stem cells from related donors with one fully mismatched HLA haplotype," N. Eng. J. Med., vol. 339, pp. 1186-1193 (1998).
Gandy et al., "CD8+TCR+ and CD8+TCR− cells on whole bone marrow facilitate engraftment of hematopoietic stem cells across allogeneic barriers," Immunity, vol. 11, pp. 579-590 (1999).

(Continued)

*Primary Examiner* — Quang Nguyen
(74) *Attorney, Agent, or Firm* — Jenkins, Wilson, Taylor & Hunt, P.A.

(57) ABSTRACT

The present invention relates to the use of a composition containing stem cells as well as CD6 depleted stem cells for the induction of a tolerance to allogenic transplants and/or for the treatment of blood, immune, and cancer diseases for time-staggered application wherein first the stem cells are applied followed by application of the CD6 depleted stem cells. Furthermore, the present invention relates to a compound preparation containing stem cells and CD6 depleted stem cells.

14 Claims, 3 Drawing Sheets

(56) References Cited

OTHER PUBLICATIONS

Guinan et al., "Transplantation of anergic histoincompatible bone marrow allografts," N. Eng. J. Med., vol. 340, pp. 1704-1714 (1999).
Handgretinger et al., "Transplantation of megadoses of purified haploidentical stem cells,"Ann. N. Y. Acad. Sci. vol. 872, pp. 351-361; discussion 361-362 (Apr. 30, 1999).
Marmont et al., "T-cell depletion of HLA-identical transplants in leukemia," Blood, vol. 78, pp. 2120-2130 (1991).
Martin et al., "Involvement of donor T-cell effector mechanism in preventing allogeneic marrow graft rejection," Blood, vol. 92, pp. 2177-2181 (1998).
Mavroudis et al., "Effect of CD34 cell dose on outcome following T-depleted marrow transplantation," Blood, vol. 88, pp. 3223 (1996).
Paulin, T., "Importance of bone marrow cell dose in bone marrow transplantation," Clin. Transplant, vol. 6, p. 48 (1992).
Reich-Zeliger et al., "Anti-Third Party CD8+ CTLs as Potent Veto Cells: Coexpression of CD8 and FasL is a prerequisite," Immunity, vol. 13, pp. 507-515 (2000).
Schumm et al., "Prevention of Graft-versus-Host disease in DLA-haplotype mismatched dogs and hemopoietic engraftment of CD6 depleted marrow with and without cGCSF treatment after transplantation," Tissue antigens, vol. 43, pp. 170-178 (1994).
Shapiro et al., "Bone marrow augmentation in renal transplant recipients," Transplant Proc., vol. 30, pp. 1371-1374 (1998).
Sykes et al., "Mixed lymphohematopoietic chimerism and graft-versus-lymphoma effects after non-myeloablative therapy and HLA-mismatched bone marrow transplantation," Lancet, vol. 358, pp. 1755-1759 (1999).

* cited by examiner

USE OF STEM CELLS AND CD6 DEPLETED STEM CELLS FOR THE INDUCTION OF TOLERANCE TO ALLOGENIC TRANSPLANTS AND/OR FOR THE TREATMENT OF LEUKEMIA

RELATED APPLICATIONS

This application is a continuation of PCT patent application number PCT/EP01/11776, filed Oct. 11, 2001, which claims priority to German patent application number 10050334.9, filed Oct. 11, 2000, the disclosures of each of which are incorporated herein by reference in their entirety.

TECHNICAL FIELD

The present invention relates to the use of a composition containing stem cells as well as CD6 depleted stem cells for the induction of tolerance to allogenic transplants and/or for the treatment of blood, immune, and cancer diseases for time-staggered application wherein first the stem cells are applied followed by application of the CD6 depleted stem cells. Furthermore, the present invention relates to a compound preparation containing stem cells and CD6 depleted stem cells.

BACKGROUND OF THE INVENTION

The transplantation of hematopoietic stem cells and bone marrow belongs to the prior art. This technique includes first a destruction of immunocompetent cells of the recipient by a pretreatment such as by means of chemotherapy or radiotherapy to an extent sufficient to enable growth of the donor cells including stem cells and immunocompetent cells. Generally, stem cells transplantation is used in the case of diseases accompanied by a functional loss of the bone marrow for example in the frame of the therapy of acute leucemia but also for other blood and immune diseases as well as for cancer diseases. This range of diseases to be treated is due to the fact that these are all diseases based on a malfunction in hematopoiesis. Thus, stem cells may be used for non-malignant blood disorders (such as severe aplastic anemia (SAA), aplastic anemia, sickle cell anemia, thalassemia), immune system disorders (multiple sclerosis (MS), rheumatic diseases (CP), scleroderma) as well as for malignant blood disorders (acute and chronic leucemias of myeloid and lymphatic origin). For this purpose, preparations containing stem cells such as bone marrow and blood leucocytes are usually obtained from the donor and administered to the recipient intravenously. A stem cell transplantation of this type can induce tolerance to organs such as heart, lung etc. as well as to blood stem cells of the stem cells donor (1). A disadvantage of this type of stem cell transplantation is, however, that on the one hand the patient transplant may be rejected and on the other hand immunocompetent cells of the transplant may attack and injure cells of the recipient in the course of a graft-versus-host (GVH) disease wherein T cells of the transplant recognize cells of the recipient as non-self. In contrast to the transplantation of solid organs, the immunosuppressive treatment may be discontinued after months or years in the case of a stem cell transplantation if no rejection or GVH reaction occurs. A mutual tolerance is assumed.

To prevent or decrease, respectively, the graft-versus-host reaction, immunocompetent cells, particularly T lymphocytes are frequently removed from the transplant. This, however, quite often results in transplant rejection (2), and in the case of the treatment of leucemia recurrences of the disease increasingly occur. The recurrences in the case of leucemia treatment as well as transplant rejection presumably occur due to a lack of donor T cells in the transplant which would be able to eliminate the T cells remaining after pretreatment of the recipient (3). Such complications do indeed bear a rather high risk even in the case of HLA identity (identity of tissue features) between donor and recipient and a very high risk for HLA differences.

Stem cell transplantation for the induction of a tolerance to transplants or for maintaining the tolerance was initially done based on the consideration that the patient's immune system will be replaced by the immune system of the stem cell donor which does not attack the transplanted organ. Therefore, as soon as an organism has accepted foreign stem cells this organism also will take other organs (4). Since, however, stem cell transplantation across HLA differences bear a high risk this method for the induction of tolerance to transplanted organs is not useful at the moment.

It has been demonstrated in dogs that in special donor-recipient combinations a strong graft-versus-host reaction can be avoided by T cell depletion of the bone marrow. In combinations of DLA homozygous donors and DLA heterozygous recipients the reaction in host-versus-graft direction is weak compared to the GVH direction, a complete chimerism is obtained with sustained tolerance across differences in DLA haplotype (5). Strong DLA differences, however, of the heterozygous donor almost always result in rejection and do not allow for mutual tolerance.

There have already been various attempts and possibilities for the prevention or reduction, respectively, of a rejection due to HLA differences.

For example it is known that the use of high amounts of CD34-positive blood stem cells may induce tolerance in adults (6) and children (7). In the case of adult donors and small recipients as often encountered in parent-to-children transplantations blood stem cells may be obtained in sufficient amounts. If the size relations are more unfavorable it will be problematic to obtains blood stem cells in sufficient amounts.

As another method for the induction of tolerance across HLA differences there has been suggested bone marrow transplantation together with a combination of cyclophosphamide, thymus irradiation and anti-thymocyte globulin (ATG) (8). This procedure has been successful for patients with highly malignant lymphoma but these patients are already immunosuppressed due to their diseases and the preceding chemotherapy. It can be assumed, however, that this type of treatment would not be sufficient for patients with a weaker previous immunosuppression. A further disadvantage of this method is an increased susceptibility of the organism to infections as with all merely unspecific immunosuppressive agents.

Another method is the use of CTLA4, a ligand of the B7.1 co-stimulatory molecule. Among other properties, CTLA4 limits T cell activation on antigen stimulation. The expression of the co-stimulatory molecule B7.1 on antigen-presenting cells is necessary for T cell activation. In the above-mentioned method, CTLA4-IgG fusion protein is added to the bone marrow prior to transplantation where it blocks the B7.1 co-stimulatory molecule, and thus the recipient T cells lack the second signal important for activation. The T cells are unable to react ('anergy') and their capability to perform an acute graft-versus-host reaction is decreased (9). This method has been tested in twelve patients, four patients of which were in a group with good risk and eight patients in a group with increased risk. "Good risk" refers to young patients, little therapy attempts, a low amount of leucemic cells and outbreak of the diseases not long ago while these conditions do not apply in the case of a "high risk". In this method, however, the irradiated blood cells of the recipient must be treated over an incubation period of 36 hours. Besides an increased risk of infection, an increased risk of tolerance induction can be expected.

SUMMARY OF THE INVENTION

It is an object of the present invention to enable stem cell transplantation also across HLA differences to on the one hand ensure a stem cell transplantation also for patients without matching HLA-identical donor—up to now only possible with little success and accompanied by the disadvantages mentioned above—and on the other hand to induce tolerance to transplanted organs which are almost always derived from HLA-differing donors. It is another object to provide a preparation for this purpose.

This object is achieved by the use of stem cells and CD6 depleted stem cells according to claim 1 as well as by a compound preparation according to claim 13. Preferred embodiments of the invention become obvious from the dependent claims.

TABLES

Tab. 1 shows the growth behavior of stem cells in HLA haploidentical transplantation and the graft-versus-host disease for various HLA differences in stem cell transplantations according to the invention and stem cell transplantations according to the prior art. Tabs. 2 and 3 show patient data and therapy results of patients treated according to the invention. Tab. 4 shows the phenotype and the composition, respectively, of PBSCs after CD6 depletion of various cell preparations. Tab. 5 shows the suppression of the MLR by various cell preparations. Tab. 6 shows the suppressor activity of MLR of various cell preparations.

DETAILED DESCRIPTION OF THE PRESENT INVENTION

According to the present invention there is used a composition containing stem cells and CD6 depleted stem cells for time-staggered application, for the induction of tolerance to allogenic transplants and/or for the treatment of leucemia, blood, immune and/or cancer diseases wherein first the stem cells and then the CD6 depleted stem cells are administered. Preferably the CD6 depleted stem cells are applied four to eight days, mostly six days after stem cell transplantation. The combination of stem cells and CD6 depleted stem cells i.a. has the advantage of enabling transplantation of a large amount of stem cells due to the twofold application.

According to the present invention the stem cells may be derived from bone marrow, peripheral blood or umbilical cord blood. These different types of stem cells may be combined according to the invention with similar or different CD6 depleted types of stem cells. For example bone marrow stem cells may be applied first followed by CD6 depleted bone marrow stem cells, CD6 depleted peripheral blood stem cells and/or CD6 depleted umbilical cord blood stem cells. Similarly, also all other combinations are contemplated according to the invention. Preferred are the combinations: bone marrow stem cells—CD6 depleted bone marrow stem cells, bone marrow stem cells—CD6 depleted peripheral blood stem cells, peripheral blood stem cells—CD6 depleted peripheral blood stem cells, peripheral blood stem cells—CD6 depleted bone marrow stem cells, or umbilical cord blood stem cells—CD6 depleted umbilical cord blood stem cells.

Also according to the invention stem cells derived from different sources may be present within a transplant, i.e. also a mixture of for example bone marrow stem cells and peripheral blood stem cells may be applied followed by a mixture of CD6 depleted bone marrow stem cells and CD6 depleted peripheral blood stem cells. Also in this case any combination is comprised by the present invention.

According to the invention the term stem cells is used to refer to stem cell preparations or preparations enriched in stem cells or stem cell rich preparation. Bone marrow for example is a "stem cell rich preparation". According to the invention, the term bone marrow may be used synonymously to bone marrow stem cells. Therefore, according to the invention it is also possible to pretreat the bone marrow prior to transplantation in a manner to remove red blood cells.

Peripheral blood stem cells according to the invention refers to those stem cells present in the periphery. By administration of at least one cellular growth factor (e.g. G-CSF, i.e. granulocyte colony stimulating factor, or GM-CSF) the mobilization of stem cells from bone marrow into the blood can be achieved, a behavior which they also show naturally in the frame of severe infections and blood loss.

Umbilical cord blood stem cells according to the invention refers to such stem cells obtained by means of puncture after cutting the umbilical cord of a newborn child.

It is known that a larger number of stem cells is accompanied by a better success of allogenic transplantation (10-13). Since in the present invention, an application of stem cells is performed twice each in an amount which is typically used also otherwise in stem cell transplantations the efficiency of the method according to the invention is affected in a positive manner.

Due to the time-staggered application according to the invention of stem cells followed by stem cells showing a depletion in CD6-positive cells the stem cell preparation is first enabled to grow. Growth or take means that the stem cells applied intravenously bind within the bone marrow with their homing receptors, divide and initiate the production of cells.

Generally, transplant rejection does not occur before several days following a stem cell transplantation due to the initiation of an immune response. For the suppression and/or prevention of this immune response the CD6 depleted stem cells are administered according to the invention. These have an immunemodulatory effect. In the case of a HLA difference between donor and recipient, activated lymphocytes may occur already during the first six days leading to rejection or GVH reaction, respectively. If CD6 depleted stem cells are added according to the invention such activated cells may be recognized at that time and eliminated without any deleterious effect on the stem cells of the donor.

It has been found in the context of the present invention that stem cell preparations with a depletion in CD6-positive T cells have the effect of unspecifically eliminating activated lymphocytes in their amount/proliferation. Up to now not much is known about the biological function of the CD6 antigen. It is a ligand for AL-CAM (activated lymphocyte cell adhesion molecule), the marker of activated lymphocytes. Following a depletion of CD6-positive T cells almost all CD4-positive (e.g. helper T cells) and most of the CD8-positive T cells (e.g. cytotoxic T cells) are eliminated while natural killer (NK) cells are still present.

The depletion of CD6-positive T cells has been established since some time in individual centers for a prophylaxis of the GVH disease, whereby the GVH disease occurred to a decreased extent both in HLA identical (14,15) and HLA different (16) transplantations. In these procedures exclusively CD6 depleted stem cells were transplanted with the aim to largely remove T cells from the transplant by the CD6 depletion as described above. The disadvantages of a transplantation without T cells have been described in the beginning. In contrast the present invention refers to the suppressing activity of the CD6 depleted cells, i.e. the cells remaining after CD6 depletion.

Figure 1:
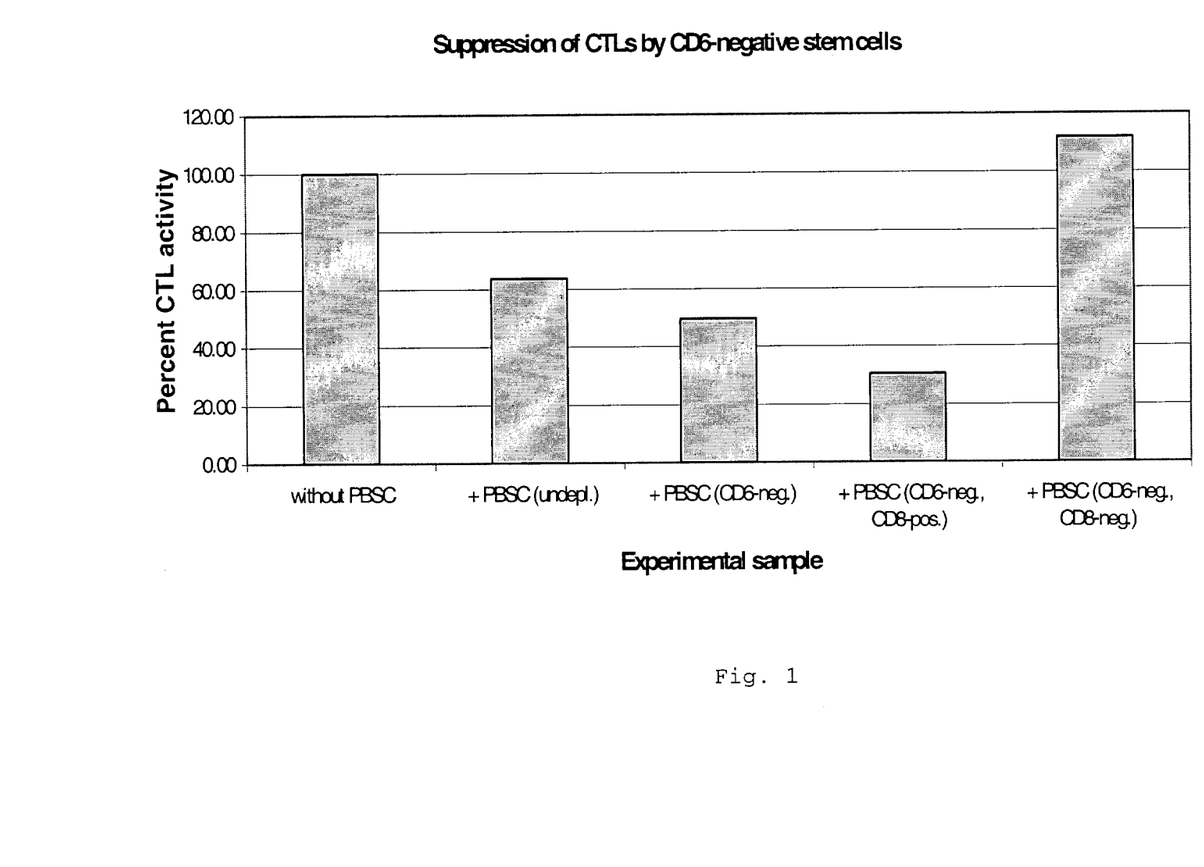
FIG. 1 shows the suppression of cytotoxic T lymphocytes (CTLs) by CD6-negative stem cells in culture samples.

It has been demonstrated according to the invention that CD6-negative stem cells in culture suppress the formation of cytotoxic T cells (see FIG. 1). FIG. 1 shows the suppression of cytotoxic T lymphocytes (CTLs) by CD6-negative stem cells in culture samples. Shown is the relative activity of cytotoxic T lymphocytes (CTL activity) for different culture samples in relation to different peripheral blood stem cell (PBSC) preparations. In a mixed lymphocyte culture, irradiated stimulator cells of a donor (B) (=without peripheral blood stem cells (PBSCs)) were added to lymphocytes of a donor (A). To this cell suspension either undepleted PBSCs, CD6 depleted PBSCs, the CD8-pos. cells of the cells remaining after CD6 depletion or both CD6 and CD8 depleted PBSCs of a donor (C) were added. After 7 and 14 days, respectively, the cultured cells were assayed for CTL activity. For this purpose, chromium-radiolabeled blasts of stimulator (B) were added to the CTLs in an effector:target ratio of 40:1, 20:1, 10:1, 5:1, and 2:1. Blasts of the effector (A) and the PBSC donor (C) served as a control. Both against (A) and (C) the CTL activity was lower than 5 percent. The CTL activity without addition of stem cells is given as 100%. If non-depleted PBSCs are added the relative CTL activity decreases to about 63%. Upon addition of CD6 depleted PBSCs the relative CTL activity decreases to about 45%. In the case of CD6 and CD8 depletion the CTL activity is increased to about 110% while the CD8-positive cells of the cells remaining after CD6 depletion result in a further reduction in CTL activity to about 30%. Depletion in NK cells does not reduce the suppressive activity. Enriched CD34-positive stem cells which are also found in the CD6 depleted fractions alone have not shown any suppressive effect. It has been shown according to the invention that CD6 depleted bone marrow and blood stem cell preparations unspecifically suppress the immune reaction to allogenic cells in vitro as well as the incorporation of $^3$H-tyhmidine in the mixed lymphocyte culture and the generation of cytotoxic T cells. The suppressing effect is mainly mediated by the CD8-positive cells remaining in the transplant after CD6 depletion.

Besides the suppressing effect of CD6 depleted stem cell preparations the time course is of importance. The CD6 depleted stem cell fraction is administered 4 to 8 days, preferably about 6 days after stem cell transplantation. At this point lymphocytes of the recipient and the donor have already been activated in the patient if there are differences between donor and patient. In culture, the CD6-negative stem cell preparations have a suppressive effect independent of the HLA type and occurring in a similar manner to cells of the donor, the patient, and a third person. The unspecific effect of the stem cell preparations to activated T cells renders individual features such as HLA antigens unlikely target structures. It is more likely that these are structures which are commonly present in the transformation of activated lymphocytes.

The present invention now enables a transplantation of stem cells and optionally also of organs even across HLA differences. Parents and offspring of the patient are haploidentical due to inheritance, i.e. one half of the HLA antigens inherited with one chromosomal piece are identical. Identities of antigens of the second HLA haplotype (usually determined are the antigens for HLA-A, -B, and -DR; an extended determination is possible but of unknown relevance to the outcome) are indiscriminate as in the case of non-relatives. On a statistical average also one half of the sisters and brothers is haploidentical, and one quarter each is HLA identical or completely different to the patient, respectively. Thus, our invention means that for practically every patient suffering from leucemia or other severe blood diseases a donor can be found within the own family. Also for organ transplantations the probablility is significantly increased if the donor matches the patient in 3 HLA antigens. Matching of more HLA antigens is advantageous since important self-structures can only be recognized if they are presented by self HLA antigens. According to the invention the HLA difference may also be more than 3, theoretically up to 6 of 6 antigens determined.

In the use according to the invention of stem cells and CD6 depleted stem cell preparations the transplant recipients undergo an immunosuppressive pretreatment with total body irradiation, chemotherapy, and antibodies. This serves to almost completely abolish hematopoiesis and the immune defense system of the recipient, moreover, the immunosuppressive effectiveness of cyclophosphamide may be specifically enhanced by transfusion of donor leucocytes prior to treatment.

The preparation of bone marrow stem cells and the preparation of blood stem cells according to the invention is performed according to the prior art. In the case of blood group incompatibilities the red blood cells are removed to prevent lysis (hemolysis). If possible the stem cells prepared should be obtained directly (up to 48 h) prior to transplantation. Should this not be possible then the stem cells may also be obtained at an earlier point and stored with a cryoprotectant (e.g. DMSO) at up to −196° C. (in the liquid or gaseous nitrogen phase) until transplantation.

According to the invention, the preparation of blood stem cells is done such that first a cellular growth factor (e.g. G-CSF) is administered to the donor for 4 to 6 days, if the number of CD34-positive stem cells is high (about >10/μl blood) blood is obtained from the donor by means of cytapheresis.

Using an antibody directed against the CD6 epitope the CD6-positive T cells are removed from the stem cell preparation. Following incubation of the cytapherisate obtained with an anti-CD6 antibody and washing off excess antibody, magnetic particles (e.g. iron particles) or alternatively high-density particles (e.g. nickel particles) are added which are bound only to the CD6 antibody. The cell-antibody suspension is passed over a magnet to which all cells become bound which carry the antibody-particle combination. CD6-positive cells loaded with density particles are separated by sedimentation. The recovery rate of the CD6-negative cells in both methods is up to 100%. If possible, the CD6 depleted stem cells should be obtained directly (up to 48 h) prior to transplantation. Should this not be possible then the stem cells may also be obtained at an earlier point and stored after separation with a cryoprotectant (e.g. DMSO) at up to −196° C. (in the liquid or gaseous nitrogen phase) until transplantation.

The amounts of stem cells applied according to the invention for the non-CD6 depleted stem cells are about $1\text{-}4\times10^8$, preferably $2\text{-}4\times10^8$ mononuclear cells/kg of body weight while as much as possible are desired. In the case of the CD6 depleted stem cells the amount is about $0.4\text{-}2.0\times10^6$, preferably $0.8\text{-}2.0\times10^6$ CD34-positive cells/kg of body weight. Also in this case an as high cell number as possible is desired.

Both the bone marrow stem cells and the blood stem cells are administered to the patient intravenously.

In the case of organ transplantation there are several possibilities of using the invention. In life donors (kidney) an immunosuppressive pretreatment similar to stem cell donors may be scheduled. Following organ donation the donor may be stimulated with growth factor and apherized after about 6 days as in a stem cell transplantation. Alternatively bone marrow may be obtained in addition. The preparations may either be transfused freshly or may be cryopreserved after preparation. For dead donors an immunosuppression can only be started at the point of transplantation while the bone marrow preparation must occur simultaneously to organ preparation. Bone marrow is cryopreserved after CD6 separation.

After the initial rejection and GVH reaction have been suppressed the tolerance is maintained by a chimerism, i.e. survival of the foreign hematopoiesis within the patient. According to the invention, blood and bone marrow stem cell preparations can also be present as a compound preparation since according to the invention no HLA identity between the CD6 depleted preparation and the organ or stem cell transplant, respectively, is required. Insofar as the HLA difference is within the tolerance range according to the invention a compound preparation can be used if necessary. If preparations of more than one donor are used the non-depleted preparation will contribute to chimerism.

Besides an induction of tolerance to allogenic transplants the invention comprises the treatment of blood, immune, and cancer diseases originating in a malfunction of hematopoiesis, for example non-malignant blood diseases (e.g. severe aplastic anemia, aplastic anemia, sickle cell anemia, or thalassemia), immune system disorders (e.g. multiple sclerosis, rheumatic diseases (CP), scleroderma), and malignant blood disorders (e.g. acute and chronic leucemias of myeloid and lymphatic origin).

In the following, the invention will be described with respect to Examples which, however, are not intended to limit the scope of the invention.

EXAMPLES

In the frame of a study according to the invention 21 patients with otherwise therapy-refractory leucemias were transplanted with a compound preparation according to the invention of bone marrow or,blood cells, respectively, and CD6 depleted blood stem cells in the context of a curing attempt. The patients were high-risk patients. For comparison purposes, patients in the same stages of leucemia were used which, however, underwent a treatment according to the prior art. A total of 5 patient groups were examined. The results are presented in Table I.

1. Preparation of Bone Marrow Stem Cells:

Following a thorough examination of the donor for suitability for donation and verification by the attending physician about 3 weeks prior to the planned bone marrow preparation, about 1000-1500 ml bone marrow depending on the cell count/ml in the bone marrow and the patient weight were removed from each donor under general anesthetic from both iliac crests and suspended in a suitable medium (e.g. RPMI 1640) containing heparin or heparin and citrate solution (ACD). In the case of blood group compatibility this bone marrow was used without further treatment. If this was not the case, erythrocyte depletion adding a sedimentation enhancer was performed by means of sedimentation or centrifugation.

2. Preparation of Blood Stem Cells:

Following a thorough examination of the donor for suitability for donation and confirmation thereof by the examining physician, the growth factor G-CSF is administered to the donor in a dosage of 5-12.5 µg/kg of body weight starting from the $5^{th}$ day prior to the planned stem cell preparation. From the $4^{th}$ day the blood of the donor is examined in the laboratory for its content in CD34-positive cell. As soon as more than 10 CD34-pos. cells/µl can be detected a leucocytopheresis is performed by means of a cell separator. During leucocytopheresis the blood is rendered unclottable outside of the donor's body using heparin and ACD. The stem cell rich leucocyte preparations are placed in a separate blood bag containing tissue culture medium (e.g. RPMI 1640) while the remaining blood is directed back into the donor. If the cell numbers obtained in this manner are not sufficient for transplantation another cytapheresis is performed on the next day if this is compatible with the physical condition of the donor.

3. Preparation of Umbilical Cord Stem Cells:

Following birth and cutting of the umbilical cord of the newborn child the umbilical cord blood which is still present in the umbilical cord and in the placenta and is very rich in stem cells is obtained by puncture of the umbilical cord vein. The umbilical cord blood thus obtained is cleared from a major portion of erythrocytes by sedimentation and subsequently a portion of the plasma is removed by sedimentation. The umbilical cord blood thus processed is split between at least two blood bags and after, addition of a cryoprotectant, is stored at $-196°$ C. until use.

4. CD6 Depletion of Stem Cells:

After washing off the thrombocytes by centrifugation, the stem cells prepared are incubated in a concentration of about $1\times10^8$ cells/ml with oversaturated concentrations ($\sim$1 mg/50$\times$ $10^8$ cells) of anti-CD6 antibody (e.g. MT404 by P. Rieber/G. Riethmüller; other anti-CD6 antibodies are possible) for 30 min at room temperature. Excess unbound antibodies are washed away by twice addition of washing medium (e.g. RPMI) and centrifugation. The separation of the CD6-positive cells is carried out with so-called immunomagnetic particles, i.e. iron particles coated with an antibody to the first antibody, e.g. a sheep anti-mouse antibody if the first antibody is derived from mouse. Thus, iron particles adhere to the surface of the CD6-positive cell and enable retaining the cell within the bag by means of a magnet. If magnetic particles are used (e.g. Dynabeads®) the blood bag is placed onto a magnet after an incubation of 30 minutes at 4° C. The CD6-negative bag content is transferred to a new bag by means of a (peristaltic) pump via a tube and a secondary magnet. This procedure is repeated once.

If high-density microparticles (e.g. nickel particles) are separated the CD6-positive cells are removed by sedimentation instead of a magnet.

After separation the cell suspension thus obtained is examined for its cell number and proportion of CD34-, CD8-, CD4-, and CD6-positive cells.

5. Patient Pretreatment:

In general the pretreatment results in a severe suppression of hematopoiesis and a deficiency in immune defense whereby leucemic cells are eliminated as much as possible and the rejection response to the foreign transplant possibly is completely suppressed.

First, patients of all groups received a total body irradiation with 4 Gy each per day on 3 successive days.

Group 1 in addition received a treatment with only cyclphosphamide (CY). For this purpose 0.50 mg CY per kg of body weight per day were administered to the patients intravenously on four successive days.

Patients of group 2 also received CY treatment as those of group 1 but on the last day of radiotherapy or on the day prior to the first CY treatment received a transfusion of donor leucocytes (DBC) administering the total amount of leucocytes obtained from the donor in the course of two hours of leucapheresis to each patient. These leucocytes result in a stimulation and proliferation of the patient's lymphocytes which recognize histocompatibility antigens of the donor. The dividing lymphocytes are particularly susceptible to the CY treatment performed on the next day.

Group 3 did not receive donor leucocytes but 20 mg/kg rabbit anti-human thymocyte globulin (ATG Fresenius®) in the morning on the days of CY treatment.

Group 4 received the same treatment as group 3 but additionally a transfusion of donor leucocytes on the day prior to the first ATG/CY treatment.

Group 5 is the group undergoing a treatment according to the present application. It received the same pretreatment as group 4 but additionally received CD6 depleted blood stem cells 6 days after stem cell transplantation.

6. Stem Cell Transplantation:

On the day of termination of the respective pretreatments $1-4 \times 10^8$ mononuclear cells per kg of body weight each were administered to the patients intravenously.

7. Transplantation of CD6 Depleted Stem Cells:

The patients of group 5 received $0.4-2 \times 10^6$ CD6 depleted, CD34-positive stem cells per kg of body weight intravenously 4 to 8 days following stem cell transplantation.

8. GVH Prophylaxis

All patients received a prophylactic immunosuppressive treatment according to the prior art with intravenous cyclosporin A from day −1 and methotrexate on days 1, 3, 6, and 7, respectively, following transplantation.

In the frame of the experimental series patients were treated according to the method of the present invention differing in several HLA antigens with their donors. If the donor has HLA antigens foreign to the patient the situation is referred to as host-versus-graft direction, i.e. in the direction of transplant rejection. If the patient has HLA antigens foreign to the donor this is referred to as a difference in graft-versus-host direction. Conventionally, a dissimilarity in one serologically defined antigen is considered as a difference. Not taken into consideration are differences on the genetic level which are nowadays assessable by DNA testing.

Example

| Donor: | | HLA patient: | |
|---|---|---|---|
| A = 2 | A = 1 | A = 2 | A = 2 |
| B = 27 | B = 5 | B = 8 | B = 27 |
| DR = 3 | DR = 3 | DR = 1 | DR = 3 | common HLA haplotype in italics
Difference in HVG direction: A1 and B5
Difference in GVH direction: B8 and DR 1

The results are presented in Table 1. In the haploidentical stem cell transplantation different transplantation models with varying conditioning were performed. Similar to all is the infusion of stem cells (bone marrow stem cells or peripheral blood stem cells) on the days of termination of the pretreatment. In groups II, IV, and V the patients receive DBC (donor leucocyte administration) following TBI (total body irradiation). Patients of group V additionally receive CD6 depleted stem cells 4-8 days after transplantation.

Column 1 describes the different treatment groups wherein groups I-IV are comparative groups to group V (transplantation according to the invention). The second column gives the number of patients transplanted in the respective group. Column 3 shows a) the number of mismatches (HLA differences), b) the number of patients transplanted with X mismatches, and c) the HLA loci to which the mismatches in HVG direction relate, i.e. the features which the recipient recognizes as foreign in the donor. In the column "Take" the number of patients is given in which growth of the transplant was confirmed. The fifth column is the same as column 3 but in view of the transplant, i.e. how many HLA features in the recipient are recognized as foreign by the transplant. The last column gives the numbers of patients in which a reaction of the transplant to the recipient was observed. From grade II on these reactions can be treated by an additional therapy. Grade IV is the most severe GVH grade with mostly lethal outcome.

Despite of gross HLA difference in the group treated according to the invention the ratio of patients in which the GVH grade is II or higher is at least comparable to the ratio of the patients treated according to the prior art. Furthermore it was observed that despite of more advanced leucemia, a higher HLA difference and lower proportion of children no inferior survival rate was observed with the treatment according to the invention. Moreover, it was unnecessary in a higher amount of cases to perform a long-lasting accompanying immunosuppression after treatment.

Tabs. 2 and 3 give more detailed information with respect to the patients listed in Tab. 1, group 5, as well as several other patients who were treated in addition.

| Abbreviations used in Tabs. 2 and 3: | |
|---|---|
| AML: | acute myeloid leucemia |
| NHL: | non-Hodgkin lymphoma |
| ALL: | acute lymphatic leucemia |
| CLL: | chronic lymphatic leucemia |
| CML: | chronic myeloid leucemia |
| T-ALL: | T cell acute lymphatic leucemia |
| sAML: | secondary AML |
| OMF: | osteomyelofibrosis |
| MDS: | myelodisplastic syndrome |
| RA: | refractory anemia |
| UPN: | unknown patient number |
| Take: | growth |

For example, "-" for patient No. 1138 means that growth has not occurred after about 8 days but later.

Further Examples

The present invention relates to the use of T suppressor cells or "facilitator cells" which not only suppress the graft-versus-host reaction but also the rejection response. These suppressor cells are CD6-negative, i.e. are not active in the presence of CD6-positive cells. Following CD6 depletion there is found an almost complete depletion in CD4-positive T cells and a marked depletion in CD8-positive T cells of which, however 4-5% are retained (Table 4). CD34-positive stem cells and CD16-positive CD56-positive so-called natural killer cells remain. The immunosuppressive effect of this CD6 depleted cell preparation was examined in the mixed lymphocyte culture ("mixed leucocyte reaction"—MLR) in which the lymphocytes of two HLA different persons are introduced into a culture dish and as a result of recognition of the different HLA-D determinants mutually initiate division. To detect the direction of the reaction, division of the cells of one of the persons is inhibited by irradiation. If bone marrow or so-called blood stem cells are added to the MLR the reaction is slightly suppressed (Table 5). If CD6 depleted cell preparations of bone marrow or so-called blood stem cells are added the reaction is markedly suppressed. Suppression of the reaction presumably occurs not due to CD34-positive stem cells since positively selected CD34-positive cells only slightly suppress the reaction (Table 5). Suppression of the MLR is largely abolished if CD8-positive cells are removed in addition to the CD6-positive cells. The assumption that CD8-positive cells which are CD6-negative are responsible for the suppression is confirmed by positive selection of CD8-positive cells from CD6-negative preparations (Table 6). While the CD8-negative subpopulation of CD6-negative cells is almost not suppressive the suppression of the CD8-positive subpopulation is impressive. In Tables 5 and 6 mean:

| cpm | counts per minute measured via incorporation of $^3$H-thymidine into cells |
|---|---|
| SI | stimulatory index (factor) |
| ARI | average relative index |
| I, II: | different experiments |

TABLE 4

HLA haploidentical Transplantation
PBSC phenotype following CD6 depletion

| | Cell type(%) | Recovery (%) | |
|---|---|---|---|
| | Mean +/− SD | Mean | Range |
| CD3+/CD4+ (n = 10) | 0.6 +/− 0.4 | 0.5 | 0.2-1.4 |
| CD3+/CD8+ (n = 10) | 4.9 +/− 4.5 | 4.1 | 0.4-15.0 |
| CD3−/CD16 or 56+ (n = 10) | 32.2 +/− 13.6 | 26.0 | 12.4-54.3 |
| CD34+ (n = 10) | 69.1 +/− 24.6 | 71.2 | 31-100 |

TABLE 5

HLA haploidentical Transplantation
PBSC phenotype after CD6 depletion

| | Mixed Leucocyte Reaction (MLR) | | | | | |
|---|---|---|---|---|---|---|
| | I | | | II | | |
| | cpm | SI | ARI | cpm | SI | ARI |
| Auto | 12,504 | 1 | 0% | 28,405 | 1 | 0% |
| Allo stim. | 44,411 | 3.6 | 100% | 47,397 | 1.7 | 100% |
| Allo stim. + BM/PBSC$_{full}$ | 19,446 | 1.6 | 21.8% | 33,241 | 1.2 | 25.5% |
| Allo stim + BM/PBSC$_{CD6-}$ | 12,646 | 1.0 | 0.45% | 25,742 | 0.9 | −14.0% |
| Allo stim + BM/PBSC$_{CD34+}$ | 34,072 | 2.7 | 67.6% | | n.d. | |
| Allo stim + BM/PBSC$_{CD6-/CD8-}$ | | n.d. | | 37,872 | 1.3 | 50% |

TABLE 6

HLA haploidentical Transplantation
Suppressor activity of MLR is in the CD6-neg. and CD8-pos. fraction

| | | cpm | SI | ARI |
|---|---|---|---|---|
| A | | 18.784 | 1 | 0% |
| A* | B | 30.258 | 1.6 | 100% |
| A* | B +PBSC | 20.031 | 1.1 | 11% |
| A* | B +PBSC CD 6⁻ | 11.070 | 0.59 | −67% |
| A* | B +PBSC CD 6⁻ 8⁺ | 8.647 | 0.46 | −88% |
| A* | B +PBSC CD 6⁻ 8⁻ | 17.970 | 0.96 | 0% |
| A | B* +PBSC CD 6⁻ 8⁻ | 29.313 | 1.6 | 44% |
| A | B* +PBSC CD 6⁻ 8⁺ | 10.519 | 0.56 | −35% |

TABLE 6-continued

HLA haploidentical Transplantation
Suppressor activity of MLR is in the CD6-neg. and CD8-pos. fraction

| | | cpm | SI | ARI |
|---|---|---|---|---|
| A | B* +PBSC CD 6⁻ | 26.361 | 1.4 | 31.6% |
| A | B* +PBSC | 29.425 | 1.6 | 44% |
| A | B* | 42.698 | 2.3 | 100% |
| B | | 18.821 | 1 | 0% |

Figure 2:
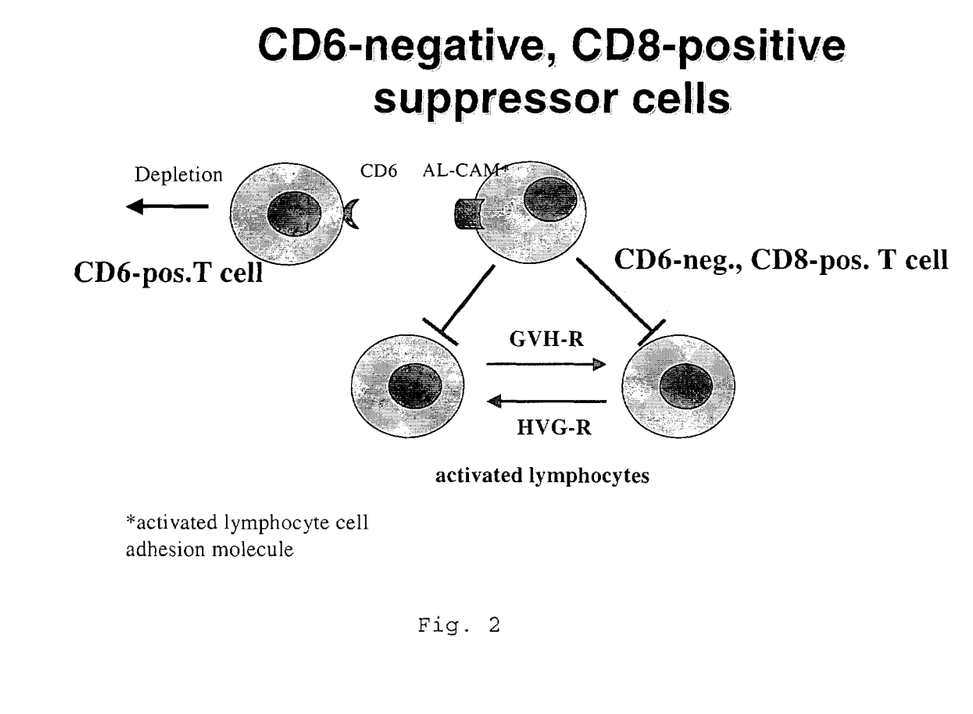
FIG. 2 shows a model for the suppression of the alloreaction by CD6-negative, CD8-positive cells.

Mechanism, Time Schedule and Advantages of the Present Invention:

The mechanism of the suppression of an immune reaction to HLA differing cells and organs is not clear up to now. All we know is that the suppression is not specific, i.e. CD6-negative, CD8-positive stem cell preparations do not only suppress the reaction of foreign lymphocytes to the body's own organs in the sense of a graft-versus-host reaction and the reaction of own lymphocytes to foreign cells and organs in the sense of a host-versus-graft or rejection response, respectively, but also the reaction between third parties. Therefore, the only possible explanation are HLA-independent reactions for example activated lymphocytes of any origin. CD8-positive suppressor cells have been described in mouse by Reich-Zeliger et al. (17) and Gandy et al. (18). Both research groups, however, have not described CD6 depletion as successful. FIG. 2 shows a model of how CD6-negative, CD8-positive cells suppress the alloreaction. The ligand for the CD6 antigen on the cell surface is ALCAM (activated leucocyte adhesion molecule), CD8-positive cells are cytotoxic cells which presumably can be cytotoxic without their specific T cell receptor in the absence of CD6-positive cells if the target cells express activation markers in the context of an immune reaction. The cytotoxicity of such cells was proven by Reisner et al. who defined FAS-L as the mediator of cytotoxicity. Since activation does not occur before several days following antigen stimulation the time-staggered administration (on the 6$^{th}$ day after transplantation) of CD6 depleted cells is implicated (time schedule of transplantation see FIG. 3).

Figure 3:
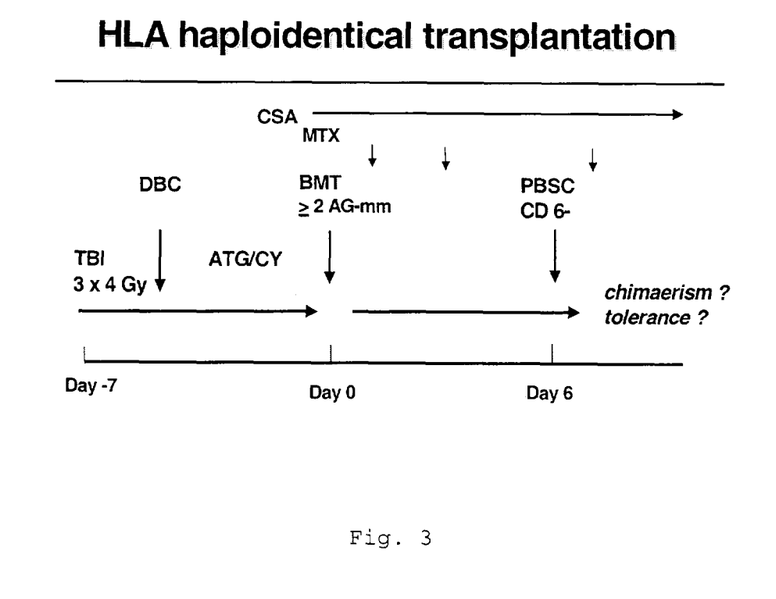
FIG. 3 is a time diagram of a preferred schedule for a transplantation according to the present invention.

| Abbreviations used in FIG. 3: | |
|---|---|
| TBI | total body irradiation |
| DBC | donor leucocytes |
| CSA | cyclosporin A |
| MTX | methotrexate |
| BMT | bone marrow transplantation |

| Abbreviations used in FIG. 3: | |
|---|---|
| ATG | anti-thrombocyte globulin |
| CY | cyclophosphamide |

The transplantation results cannot prove the mechanism but can only confirm the effect. In this respect it is of importance that our patients differ from their donors in more than one HLA antigen. In the publications of Champlin et al. (19) there is a major proportion of patients with unrelated, HLA-identical donors and related donors which are either phenotypically HLA-identical or differ only in one HLA antigen. Moreover, the work deals with the question of T cell depletion of the transplant, the comparison of depletion of all T cells to the depletion of only a part of the T cells and the transplantation of untreated preparations. It does not relate to the time-staggered transplantation of blood stem cell preparations containing suppressor cells. Another objective is concerned in (2), Craddock et al., Blood 2000; 96: 86-90. In this work donor lymphocytes are transfused at the point of a leukemia recurrence to suppress the leukemia. Also the transplantation of CD6+ T cell depleted bone marrow has already been reported by the Dana Farber Institute wherein also HLA non-identical donors were used (16). In this study, however, a CD6 depleted stem cells transplantation also was not administrated in a manner time-staggered to bone marrow transplantation. Despite of a high irradiation dosage for patient conditioning (7.5-10.5 Gy of total lymphoid irradiation and 14 Gy total body irradiation), 3 of 27 patients did not show stable growth. For patients in an early stage of the disease the two-year survival rate was 69%, and 20% for more advanced stages. In contrast our results obtained in the context of curing attempts with less irradiation and far more advanced disease stages are remarkable. The irradiation according to the invention is preferably carried out with about 4 Gy, preferably on three successive days.

According to the present invention the use of CD6 depleted blood stem cells is contemplated as well as practicable and understandable both in the HLA different transplantation of bone marrow and blood stem cells and in the transplantation of organs such as kidney and hepatic lobes. In both situations, the time of transplantation is also the time of first encounter of the different HLA antigen. This defines the time frame for a time-staggered administration of CD6 depleted blood stem cells.

REFERENCES

1. Prehn R T, Main J M: J. Natl. Cancer Inst. 18: 769-778,
2. Marmont A M, Horowitz M M, Gale R P, et al.: T-cell depletion of HLA-identical transplants in leukemia. Blood; 78: 2120-2130, 1991
3. Martin, P J, Akatsuka Y, Hahne M et al.: Involvement of donor T-cell effector mechanism in preventing allogeneic marrow graft rejection. Blood, 92, 2177-2181, 1998
4. Shapiro R, Starzl T E: Bone marrow augmentation in renal transplant recipients. Transplant Proc 30, 1371-1374, 1998
5. Schumm, M., Günther, W., Kolb, H J., Rieber, P., Büttner, M., Voss, C., Reitmeier, P., Thierfelder, S., Wilmanns, W. (1994). Prevention of Graft-versus-Host disease in DLA-haplotype mismatched dogs and hemopoietic engraftment of CD6 depleted marrow with and without cG-CSF treatment after transplantation. Tissue antigens, 43: 170-178, 1994
6. Aversa F, Tabilio A, Velardi A, Cunningham I, Terenzi A, Falzetti F, Ruggeri L, Barbabietola G, Aristei C, Latini P, Reisner Y, Martelli M F: Treatment of high-risk acute leucemia with T-cell-depleted stem cells from related donors with one fully mismatched HLA haplotype. N.Eng.J.Med. 339: 1186-1193, 1998
7. Handgretinger R, Schumm M, Lang P, Greil J, Reiter A, Bader P, Niethammer D, Klingebiel T.:Transplantation of megadoses of purified haploidentical stem cells. Ann N Y Acad Sci. Apr. 30, 1999; 872:351-61; discussion 361-2.
8. Sykes M, et al.: Mixed lymphohematopoietic chimerism and graft-versus-lymphoma effects after non-myeloablative therapy and HLA-mismatched bone marrow transplantation. Lancet 358: 1755-1759, 1999
9. Guinan E C, Boussiotis V A, Neuberg D, Brennan L L, Hirano N, Nadler L M, Gribben J G: Transplantation of anergic histoincompatible bone marrow allografts. N.Eng.J.Med. 340: 1704-1714, 1999
10. Barrett A J, Ringden O, Zhang M J, Bashey A, Cahn J Y, Cairo M S, Gale R P, Gratwohl A, Locatelli F, Martino R, Schultz K R, Tiberghien P.: Effect of nucleated marrow cell dose on relapse and survival in identical twin bone marrow transplants for leukemia. Blood. Jun. 1, 2000; 95(11):3323-7.
11. Mavroudis D, Fox M, Read E J, Carter C, Barrett A J. Effect of CD34 cell dose on outcome following T-depleted marrow transplantation. Blood. 1996;88:3223
12. Ringdén O, Nilsson B. Death by graft-versus-host disease associated with HLA mismatch, high recipient age, low marrow cell dose and splenectomy. Transplantation. 1985; 40:39
13. Paulin T. Importance of bone marrow cell dose in bone marrow transplantation. Clin Transplant. 1992;6:48
14. Soiffer R J, Ritz J: Selective T cell depletion of donor allogeneic marrow with anti-CD6 monoclonal antibody: rationale and results. Bone Marrow Transplant. 12 Suppl 3: S7-10, 1993
15. Soiffer R J, Fairclough D, Robertson M, Alyea E P, Anderson K, Freedman A S, Bartlett-Pandite L, Fisher D, Schlossman S F, Stone R, Murray C, Freeman A, Marcus K C, Mauch P, Nadler L M, Ritz J: CD-6 depleted allogeneic bone marrow transplantation for acute leucemia in first complete remission. Blood 89: 3039-3047, 1997
16. Soiffer R J, Mauch P, Fairclough D, Alyea E, Anderson K, Fisher D, Freedman A, Bartlett-Pandite L, Robertson M, Schlossman R, Gollob J, Marcus K, Murray C, Kuhlman C, Freeman A, Nadler L, Ritz J: CD6+ T cell depleted allogeneic bone marrow transplantation from genotypically HLA nonidentical related donors. Biol.Blood Marrow Transplant. 3: 11-17, 1997
17. Reich_Zeliger S, Zhao Y, Krautghamer R, Bachar-Lustig E, Reisner Y. Anti-Third Party CD8+ CTLs as Potent Veto Cells: Coexpression of CD8 and FasL is a prerequisite. Immunity 2000;13: 507-515.
18. Gandy K L, Domen J, Aguila H, Weissman I L CD8+ TCR+ and CD8+TCR– cells on whole bone marrow facilitate engraftment of hematopoietic stem cells across allogeneic barriers. Immunity 1999; 11:579-590.
19. Champlin, R. E. et al, Blood, Vol. 95, No.2 (June), 2000, 3996-4003.
20. Craddock, Ch. et al, Blood, Vol.96, No.1 (July), 2000, 86-90.

TABLE 1

HLA incompatibility, growth and graft-versus-host disease in HLA haploidentical transplantation

| Treatment group | Patients (evaluative) | Differences in HVG direction | | | | Differences in GVH direction | | | GVH ≥ grade II |
|---|---|---|---|---|---|---|---|---|---|
| | | Number of Mm | Number of pats. | locus Mm | Take | Number of Mm | Number of pats. | Locus Mm | |
| I. TBI-Cy | 6 | 0 | 1 | 1A; 4DR | 3 | 0 | 1 | 1A; 4DR | 3 |
| | | 1 | 5 | | | 1 | 5 | | |
| | | 2 | 0 | | | 2 | 0 | | |
| | | 3 | 0 | | | 3 | 0 | | |
| II. TBI-DBC-CY | 26 (25) | 0 | 3 | 5A; 2B; 8DR | 24 | 0 | 7 | 6A; 3B; 5DR | 17 |
| | | 1 | 15 | 5A, B; 1A, DR | | 1 | 14 | 1A, B; 1A, DR | |
| | | 2 | 6 | | | 2 | 2 | | |
| | | 3 | 0 | | | 3 | 0 | | |
| III. TBI-ATG-CY | 4 | 0 | 1 | 1B; 1DR | 4 | 0 | 1 | 1B; 1DR | 2 |
| | | 1 | 2 | | | 1 | 2 | | |
| | | 2 | 0 | | | 2 | 0 | | |
| | | 3 | 0 | | | 3 | 0 | | |
| IV. TBI-DBC-ATG-CY | 9 | 0 | 0 | 4A; 2B; 3DR | 9 | 0 | 0 | 4A; 2B; 3DR | 5 |
| | | 1 | 9 | | | 1 | 9 | | |
| | | 2 | 0 | | | 2 | 0 | | |
| | | 3 | 0 | | | 3 | 0 | | |
| V. TBI-DBC-ATG-CY-SC-CD6-neg. | 21 (18) | 0 | 2 | 1A; 4B; 3DR | 18 | 0 | 4 | 2A; 3B; 3DR | 12 |
| | | 1 | 8 | 2A, B; 3A, DR; 1B, DR | | 1 | 8 | 3A, B; 2A, DR | |
| | | 2 | 6 | | | 2 | 5 | | |
| | | 3 | 2 | | | 3 | 1 | | |

Abbreviations:
TBI = total body irradiation;
DBC = donor leukocytes;
CY = cyclophosphamide;
ATG = anti-thymocyte globulin;
SC = stem cells;
CD6-neg. = CD6 depleted;
HVG = host-versus-graft;
GVH = graft-versus-host;
Mm = mismatch;
A, B, DR = HLA locus

TABLE 2

CD6-depletierte Stammzellen zur Toleranz-Induktion

| UPN | Initials | Age, Sex | | Diagnosis | Stage | Cytogenetics/Subgroup | Donor | Donor Age, Sex | |
|---|---|---|---|---|---|---|---|---|---|
| 1138 | A. E. | 19.3 | f | AML | refractory | normal | mother | 44 | f |
| Zzzz | S. S. | 23.4 | f | NHL | refractory | T-NHL CD8 refr. | sister | | f |
| 1151 | W. H. | 43.2 | m | ALL | refractory | n.a. | brother | 54 | m |
| 1863 | E. M. | 51.1 | m | AML | refractory | n.a. | brother | 53 | m |
| Yyyy | N. V. T. | 39 | m | ALL | refractory | n.a. | sister | 46 | f |
| Xxxx | D. Ü. | 26.3 | f | AML | refractory | trisomy 8 | sister | 31 | f |
| 1113 | F. M. | 18.6 | m | AML | refractory | trisomy 8 | father | 49 | m |
| 1430 | M. E. | 50.4 | f | CLL | refractory | n.a. | son | 31 | m |
| 1409 | B. R. | 40.5 | f | ALL | refractory | t(9; 22) | sister | 37 | f |
| 0867 | S. M. | 53.1 | f | CML | accel. phase | t(9; 22) | nephew | 30 | m |
| 0718 | A. M. | 16.7 | m | T-ALL | refractory | Del 9 | father | 50 | m |
| 1328 | M. D. | 17.7 | m | AML | refractory | 48xy, +8 +21 | brother | 35 | m |
| 1480 | F. S. K. | 41.1 | f | sAML | refractory | monosomy 7, t(3; 3) | uncle | 65 | m |
| 1813 | S. I. | 35.9 | f | CML | 2nd blast crisis | 46, XX, t(9; 22)(q34; q11)etc. | father | 67 | m |
| 1248 | S. H. S. | 38.7 | f | AML | recidiv., chlorome | normal | brother | 37 | m |
| 0888 | M. W. F. | 50.4 | m | AML | refractory | 46 XY t(10; 12) | sister | 41 | f |
| 1812 | B. P. | 41.3 | m | AML | refractory | normal | brother | 54 | m |
| 0641 | U. V. | 39.1 | m | AML | refractory | normal | nephew | 19 | m |
| 0883 | W. A. | 19.2 | m | AML | 1st recidivation | t(9; 11) | brother | 24 | m |
| 1856 | S. F. | 48.6 | m | ALL | chemorefractory STI571 response | t(9; 22), del(7)(p15) del(7)(q11, q2?) | brother | 46 | m |
| 1796 | S. O. | 29 | m | AML | refractory | n.a. | mother | 53 | f |
| 0758 | F. H. | 39 | m | AML | refractory | del 7 | brother | 33 | m |
| 1692 | S. C. | 31.2 | m | ALL | 1st remission | t(9; 22)(q34; q11), del6(q22); | mother | 59 | f |
| 0848 | S. D. | 47.1 | f | CLL | progressing | n.a. | daughter | 19 | f |
| 1565 | B. N. | 27.1 | f | AML | refractory | normal | mother | 56 | f |
| 1338 | S. W. | 38.7 | f | AML | 1st remission | t(11; 11) | mother | 61 | f |
| 1215 | B. B. | 48.4 | f | AML/OMF | refractory | n.a. | cousin | 43 | f |
| 1184 | G. S. | 50.1 | f | MDS | RA | 5q- | son | 15 | m |

TABLE 3

CD6-depletierte Stammzellen zur Toleranz-Induktion

| UPN | Initials | Sex | Age, years | HLA Difference HVG | Take | HLA Difference GVH | Acute GVHD | Chron. GVHD | recidivation | remission period | survival period | Result |
|---|---|---|---|---|---|---|---|---|---|---|---|---|
| 1138 | A. E. | F | 19.3 | A, B | − | B, D | — | — | 0 | 8 | 8 | fungal cardiomyopathy, hemorrh. |
| Xxxx | S. S. | F | 23.4 | A, B, D | ? | A, B, C, D | — | — | 0 | 11 | 11+ | in ward |
| 1151 | W. H. | M | 43.2 | B, D | − | B, D | — | — | 0 | 15 | 15 | sepsis in panzytopenia, infection |
| 1863 | E. M | M | 51.1 | A, B, D | + | A, B, C, D | 1 | — | 0 | 18 | 18 | multi organ failure |
|  | N. V. T. | M | 39 | A, B, C, D | + | A, B, D | 4 | — | 0 | 26 | 26+ | in ward |
|  | D. Ü. | f | 26.3 | B, D | + | B, D | 3 | — | 0 | 32 | 32+ | in ward |
| 1113 | F. M. | m | 18.6 | A, D | + | A, D | 3 | — | 0 | 59 | 59 | EBV infection, ELS, |
| 1430 | M. E. | f | 50.4 | B | + | B | 2 | — | 0 | 70 | 70 | sudden respiratory failure |
| 1409 | B. R. | f | 40.5 | A, D | + | D | 3 | — | 1 | 63 | 86 | recidivation, sepsis, pneumona |
| 0867 | S. M. | f | 53.1 | — | + | A | 2 | — | 0 | 91 | 91 | AGVH, CMV-IP, bronchopneumonia |
| 0718 | A. M. | m | 16.7 | A, B, D | + | — | 3 | — | 1 | 75 | 91 | recidivation |
| 1328 | M. D. | m | 17.7 | D | + | D | 3 | — | 1 | 75 | 97 | recidivation Leakage pulmonary |
| 1480 | F. S. K. | f | 41.1 | D | + | — | 2 | 0 | 0 | 102 | 102 | mykoplasmic meningitis |
| 1813 | S. I. | f | 35.9 | A, D | + | A, C, D | 2 | 1 | 0 | 118 | 118 | V.a. cerebral EBV lymphoma |
| 1248 | S. H. S. | f | 38.7 | B | + | B | 0 | 0 | 0 | 131 | 131 | stomatitis, CMV pneumonia, sepsis |
| 0888 | M. W. F | m | 50.4 | A, B | + | A, B | 2 | 1 | 0 | 142 | 142 | CMV infection, sepsis |
| 1812 | B. P. | m | 41.3 | A, B | + | A, B | 3 | 1 | 1 | 98 | 177 | recidivation |
| 0641 | U. V. | m | 39.1 | B, C | + | A, B, C | 0 | 0 | 1 | 91 | 249 | recidivation |
| 0883 | W. A. | m | 19.2 | A | + | A | 1 | 0 | 1 | 226 | 273 | recidivation, sepsis |
| 1856 | S. F. | m | 48.6 | A, B, D | + | B, D | 0 | 0 | 0 | 338 | 338+ | lives in remission |
| 1796 | S. O. | m | 29 | — | + | A | 0 | 0 | 1 | 175 | 359 | recidivation |
| 0758 | F. H. | m | 39 | B, D | + | — | 2 | 0 | 1 | 316 | 387 | recidivation |
| 1692 | S. C. | m | 31.2 | A, B | + | A, B | 1 | 0 | 0 | 549 | 549+ | lives in remission |
| 0848 | S. D. | f | 47.1 | D | + | D | 1 | 0 | 1 | 565 | 608 | recidivation |
| 1565 | B. N. | m | 27.1 | A, B, D | + | A, B, D | 3 | 2 | 0 | 747 | 747+ | lives in remission |
| 1338 | S. W. | m | 38.7 | B | + | B | 0 | 0 | 0 | 1026 | 1026+ | lives in remission |
| 1215 | B. B. | f | 48.4 | A, D | + | A, D | 2 | 1 | 0 | 1201 | 1201+ | lives in remission |
| 1184 | G. S. | f | 50.1 | — | + | — | 0 | 0 | 0 | 1223 | 1223+ | lives in remission |

What is claimed is:

1. A method for inducing tolerance to an allogenic transplant in a subject, the method comprising:
    (a) pre-treating the subject with an immunosuppressive treatment comprising administering total body irradiation, cyclophosphamide treatment, and anti-thymocyte globulin to the subject, wherein the total body irradiation comprises exposure of the subject to about 4 Gy for each of three successive days;
    (b) administering to the subject a first preparation comprising a first plurality of stem cells, wherein the first plurality of stem cells are obtained from bone marrow, peripheral blood, umbilical cord, or a combination thereof, and wherein the first plurality of stem cells comprises CD6-positive cells;
    (c) obtaining a second preparation, wherein the obtaining comprises:
        (i) contacting a second plurality of stem cells obtained from bone marrow, peripheral blood, umbilical cord, and or a combination thereof with an antibody that binds to CD6-positive cells present within the second plurality of stem cells; and
        (ii) removing the CD6-positive cells from the second plurality of stem cells; and
    (d) administering the second preparation to the subject subsequent to administering the first preparation,
    wherein the allogenic transplant comprises the first plurality of stem cells and the second plurality of stem cells, and further wherein the first plurality of stem cells and the second plurality of stem cells differ from the subject in up to 6 HLA antigens, whereby tolerance to an allogenic transplant in the subject is induced.

2. The method according to claim 1, wherein said second preparation is administered 4-8days after administration of the first preparation.

3. The method according to claim 1, wherein a magnetic particle is bound to the antibody, and the CD6-positive T cells are removed using a magnet.

4. The method according to claim 1, wherein a density particle is bound to the antibody, and the CD6-positive T cells are removed by sedimentation.

5. The method according to claim 1, wherein said first preparation and said second preparation are administered intravenously.

6. The method according to claim 1, wherein the administered first preparation comprises $1-4\times10^8$ mononuclear cells per kg of body weight of the subject.

7. The method according to claim 1, wherein the administering is of at least one of the following combinations of first and second preparations:
    (i) a first preparation comprising a first plurality of bone marrow stem cells and a second preparation comprising a second plurality of bone marrow stem cells;
    (ii) a first preparation comprising a first plurality of bone marrow stem cells and a second preparation comprising a second plurality of peripheral blood stem cells;
    (iii) a first preparation comprising a first plurality of peripheral blood stem cells and a second preparation comprising a second plurality of peripheral blood stem cells;

(iv) a first preparation comprising a first plurality of peripheral blood stem cells and a second preparation comprising a second plurality of bone marrow stem cells; or (v) a first preparation comprising a first plurality of umbilical cord blood stem cells and a second preparation comprising a second plurality of umbilical cord blood stem cells.

8. The method according to claim 1, wherein the first plurality of stem cells and the second plurality of stem cells are from different donors.

9. The method according to claim 2, wherein said second preparation is administered 6 days after administration of the first preparation.

10. The method according to claim 1, wherein the first plurality of stem cells and the second plurality of stem cells differ with respect to the subject in 0 to 3 HLA antigens.

11. The method according to claim 6, wherein the administered first preparation comprises $2\text{-}4\times10^8$ mononuclear cells per kg of body weight of the subject.

12. The method according to claim 6, wherein the administered second preparation comprises $0.4\text{-}2\times10^6$ CD34-positive stem cells per kg of body weight of the subject.

13. The method according to claim 12, wherein the administered second preparation comprises $0.8\text{-}2\times10^6$ CD34-positive stem cells per kg of body weight of the subject.

14. A method for inducing tolerance to an allogenic transplant in a subject, the method comprising:

(a) pre-treating the subject with an immunosuppressive treatment comprising administering total body irradiation, cyclophosphamide treatment, and anti-thymocyte globulin to the subject, wherein the total body irradiation comprises exposure of the subject to 4 Gy for each of three successive days;

(b) administering to the subject a first preparation comprising a first plurality of stem cells, wherein the first plurality of stem cells are obtained from bone marrow, peripheral blood, umbilical cord, or a combination thereof, and wherein the first plurality of stem cells comprises CD6-positive cells;

(c) obtaining a second preparation, wherein the obtaining comprises:

(i) contacting a second plurality of stem cells obtained from bone marrow, peripheral blood, umbilical cord, and or a combination thereof with an antibody that binds to CD6-positive cells present within the second plurality of stem cells; and (ii) removing the CD6-positive cells from the second plurality of stem cells; and (d) administering the second preparation to the subject subsequent to administering the first preparation, wherein the allogenic transplant comprises the first plurality of stem cells and the second plurality of stem cells, and further wherein the first plurality of stem cells and the second plurality of stem cells differ from the subject in up to 6 HLA antigens, whereby tolerance to an allogenic transplant in the subject is induced.

* * * * *

UNITED STATES PATENT AND TRADEMARK OFFICE
CERTIFICATE OF CORRECTION

PATENT NO. : 8,562,968 B2  
APPLICATION NO. : 10/410852  
DATED : October 22, 2013  
INVENTOR(S) : Günther et al.

Page 1 of 1

It is certified that error appears in the above-identified patent and that said Letters Patent is hereby corrected as shown below:

On title page, item 73 Assignee
replace "GSF-Forschungszentrum für Umwelt und Gesundheit, GmbH"
with --Helmholtz Zentrum München Deutsches Forschungszentrum für Gesundheit und Umwelt GmbH--.

Signed and Sealed this
Eighteenth Day of March, 2014

Michelle K. Lee
*Deputy Director of the United States Patent and Trademark Office*